United States Patent
Shoykhet et al.

(10) Patent No.: US 10,281,058 B2
(45) Date of Patent: May 7, 2019

(54) UNINTERRUPTED FLUID FLOW WHILE MODULATING FLUID

(71) Applicant: Agilent Technologies, Inc., Santa Clara, CA (US)

(72) Inventors: Konstantin Shoykhet, Karlsruhe (DE); Klaus Witt, Keltern (DE); Stephan Buckenmaier, Ettlingen (DE); Dwight Stoll, St. Peter, MN (US)

(73) Assignee: AGILENT TECHNOLOGIES, Santa Clara, CA (US)

( * ) Notice: Subject to any disclaimer, the term of this patent is extended or adjusted under 35 U.S.C. 154(b) by 0 days.

(21) Appl. No.: 14/975,342

(22) Filed: Dec. 18, 2015

(65) Prior Publication Data
US 2016/0334031 A1  Nov. 17, 2016

(30) Foreign Application Priority Data
Dec. 12, 2014 (GB) .................................. 1422161.8

(51) Int. Cl.
| | | |
|---|---|---|
| B01D 15/14 | (2006.01) | |
| G01N 30/20 | (2006.01) | |
| G01N 30/46 | (2006.01) | |
| F16K 99/00 | (2006.01) | |
| G01N 30/32 | (2006.01) | |
| B01D 15/18 | (2006.01) | |

(Continued)

(52) U.S. Cl.
CPC .......... *F16K 99/0028* (2013.01); *B01D 15/10* (2013.01); *B01D 15/1878* (2013.01); *B01L 3/50273* (2013.01); *G01N 27/44791* (2013.01); *G01N 30/32* (2013.01); *G01N 30/465* (2013.01); *B01D 15/40* (2013.01); *B01L 2400/0475* (2013.01); *F16K 2099/0084* (2013.01); *G01N 2030/202* (2013.01); *G01N 2030/328* (2013.01)

(58) Field of Classification Search
None
See application file for complete search history.

(56) References Cited

U.S. PATENT DOCUMENTS

| | | |
|---|---|---|
| 7,036,526 B1 | 5/2006 | Dehmer |
| 2006/0186028 A1 | 8/2006 | Hughes |

(Continued)

FOREIGN PATENT DOCUMENTS

| | | |
|---|---|---|
| EP | 1577012 A1 | 9/2005 |
| EP | 2706352 A1 | 3/2014 |

(Continued)

OTHER PUBLICATIONS

Extended European Search Report dated Apr. 5, 2016 for Application No. EP15199320.

*Primary Examiner* — Paul S Hyun

(57) ABSTRACT

A fluid processing device (10) for processing fluid, wherein the fluid processing device (10) comprises a first fluid drive unit (20) configured for driving a first fluid along a first flow path (85), a second fluid drive unit (20') configured for driving a second fluid along a second flow path (86), and a fluidic switch (90) fluidically coupled to the first flow path (85) and to the second flow path (86) and configured for being switchable for transferring first fluid from the first flow path (85) into the second flow path (86) without interruption of fluid flow along at least one of the first flow path (85) and the second flow path (86).

18 Claims, 6 Drawing Sheets

(51) Int. Cl.
*B01D 15/10* (2006.01)
*B01L 3/00* (2006.01)
*G01N 27/447* (2006.01)
*B01D 15/40* (2006.01)

(56) References Cited

U.S. PATENT DOCUMENTS

2009/0126466 A1\* 5/2009 Gilar ................ B01D 15/1878
73/61.55
2013/0167193 A1 11/2013 Witt et al.

FOREIGN PATENT DOCUMENTS

| WO | 2013167193 | A1 | 11/2013 |
| WO | 2014015049 | A2 | 1/2014 |
| WO | 2014199201 | A1 | 12/2014 |

\* cited by examiner

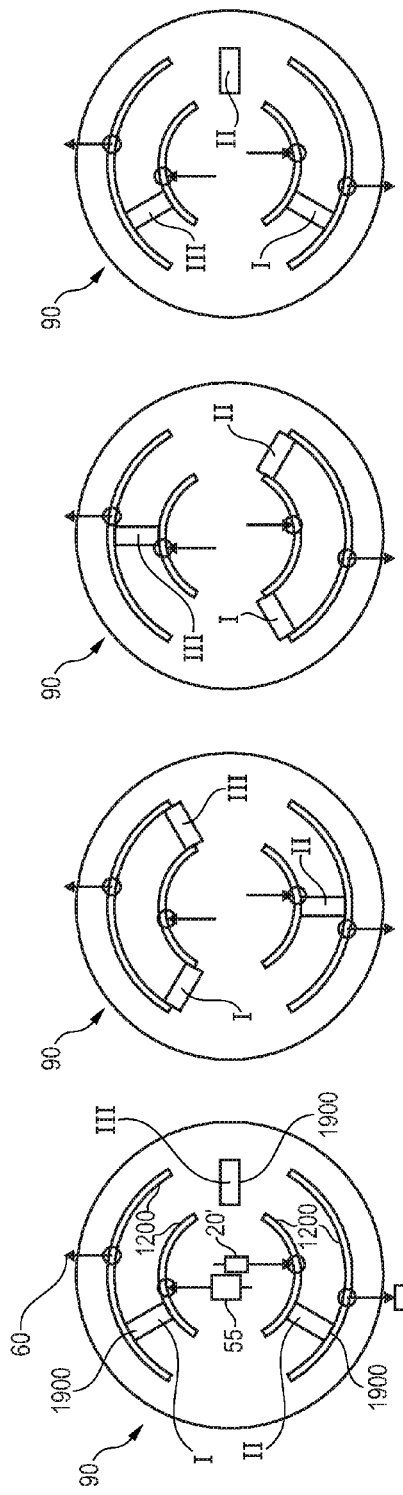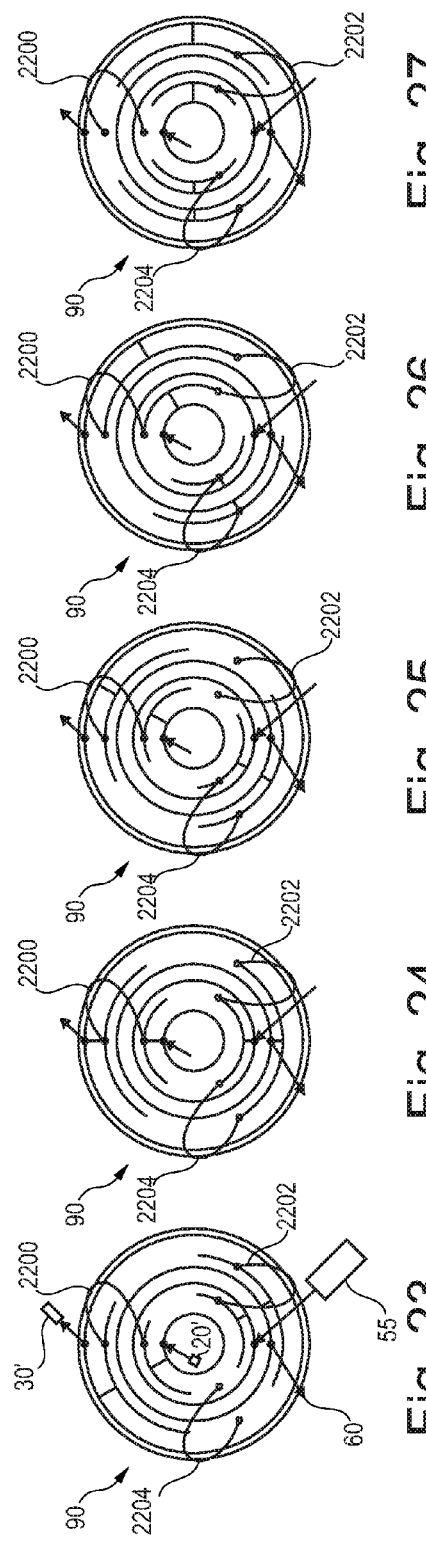

UNINTERRUPTED FLUID FLOW WHILE MODULATING FLUID

BACKGROUND ART

The present invention relates to a fluid processing device, and a method of processing fluid.

In liquid chromatography, a fluidic sample and an eluent (liquid mobile phase) may be pumped through conduits and a column in which separation of sample components takes place. The column may comprise a material which is capable of separating different components of the fluidic sample. Such a packing material, so-called beads which may comprise silica gel, may be filled into a column tube which may be connected to other elements (like a sampler having a fluidic valve, a detector) by conduits.

One or more fluidic valves may form part of a liquid chromatography apparatus. An example for such a valve for liquid separation is disclosed in U.S. Pat. No. 7,036,526 B1. Further reference is made to patent applications with U.S. application No. 61/834,883 and PCT application number PCT/IB2013/054885 published after the priority date of the present application.

US 2006/0186028 A1 discloses a liquid chromatography system for a mass spectrometer. The liquid chromatography system comprises a precolumn and an analytical column. A liquid flow through both of the precolumn and the analytical column may be adjusted by two valves. By switching the valves, the liquid chromatography system can be operated in different operational modes, wherein the precolumn and the analytical column are assigned to different flow paths in the different operational modes.

WO 2013/167193 A1 discloses a sample separation apparatus for separating a fluidic sample. The sample separation apparatus comprises a first pump delivering a first fluid to a first dimension chromatographic column. After passing the first chromatographic column, the first fluid enters a fluidic valve and a flow coupler. Further, a second fluid is delivered by a second pump. Within the fluidic valve and/or within the flow coupler, the first fluid and the second fluid are mixed to a uniform flow. Then, the uniform flow of first fluid and second fluid is delivered to a second dimension chromatographic column.

Two-dimensional separation of a fluidic sample denotes a separation technique in which a first separation procedure in a first separation unit is performed to separate a fluidic sample into a plurality of fractions, and in which a subsequent second separation procedure in a second separation unit is performed to further separate at least one of the plurality of fractions into sub-fractions. Two-dimensional liquid chromatography (2D LC) may combine two liquid chromatography separation techniques and plot the time dependency of detection events along two orthogonal time axes.

For sample separation devices such as liquid chromatography devices, fluidic switches are used. During a switching operation, pressure shocks may occur which may damage fluidic members of the sample separation device.

DISCLOSURE

It is an object of the invention to suppress pressure shocks or pressure fluctuations, which may deteriorate the integrity of fluidic members of a fluid processing device, during fluid processing. The object is solved by the independent claims. Further embodiments are shown by the dependent claims.

According to an exemplary embodiment of the present invention, a fluid processing device for processing fluid (i.e. a liquid and/or a gas, optionally comprising solid particles) is provided, wherein the fluid processing device comprises a first fluid drive unit (such as a first pump, in particular a high pressure pump; however, the first fluid drive unit may also comprise or be a reactor tank or a pipe) configured for driving a first fluid along a first flow path, a second fluid drive unit (such as a second pump, in particular a further high pressure pump) configured for driving a second fluid along a second flow path (wherein the second flow path may be at a different pressure level than the first flow path), and a fluidic switch fluidically coupled to the first flow path and to the second flow path and configured for being switchable (for instance under control of a control unit of the fluid processing device, such as a processor) for transferring first fluid (for instance for subsequently transferring individual packets of first fluid) from the first flow path into the second flow path without interruption of (i.e. continuously maintaining) fluid flow along at least one of the first flow path and the second flow path (in particular along the first flow path and along the second flow path (more particularly without pressure fluctuations or pressure shocks)).

According to another exemplary embodiment of the present invention, a method of processing fluid is provided, wherein the method comprises driving a first fluid along a first flow path, driving a second fluid along a second flow path (which may always remain separate from the first flow path), and switching a fluidic switch, being fluidically coupled to the first flow path and to the second flow path, for transferring first fluid from the first flow path into the second flow path without interruption of fluid flow along at least one of the first flow path and the second flow path (in particular along the first flow path and along the second flow path).

According to an exemplary embodiment of the invention, a fluid processing device is provided that can be operated for transferring fluid from one flow path into another flow path via a fluidic switch acting as a transfer member without the risk of pressure shocks such as a sudden pressure increase or a sudden pressure drop during a switching operation of the fluidic switch (which may be embodied as at least one fluidic valve). This can be accomplished by configuring the fluidic switch in such a way that even during the process of transferring first fluid from the first flow path into the second flow path via the fluidic switch, fluid flow interruption takes place in neither the first flow path, nor the second flow path. Therefore, sensitive fluidic members of the fluid processing device (for instance a detector such as a fluorescence detector downstream of the first fluid drive unit and upstream of the fluidic switch) are safely prevented from damage due to excessive pressure. Also the separation or detection accuracy may be reduced by such excessive pressure. It is believed that such an excessive pressure may conventionally evolve when, during switching of a fluidic switch, the fluid flow along the first flow path or along the second flow path is temporarily interrupted at any point within the respective flow path while the fluid drive unit in the respective flow path continues to pump and delivers a fluid along the flow path. Such time intervals, in which a flow path is temporarily incapable of transmitting fluid, may be rendered impossible by the configuration of the fluidic switch according to an exemplary embodiment which never interrupts the fluid flow along at least one of the first flow path and the second flow path.

In the following, further exemplary embodiments of the fluid processing device and the method will be explained.

According to an exemplary embodiment of the invention, the first flow path and the second flow path are fluidically decoupled from each other over their entire lengths (i.e. their entire courses), except within the fluidic switch, thereby allowing a transfer of fluid from the first fluid path into the second fluid path only within the fluidic switch. In particular, the course of the first fluid path may include the first fluid drive unit, a first separating unit, the fluidic switch, and a waste arranged downstream the fluidic switch. More particularly, the course of the second fluid path may include the second fluid drive unit, the fluidic switch, a second separating unit and a further waste. In other words, the first flow path meets the second flow path exclusively within the fluidic switch according to the described embodiment. That is, the only fluidic coupling of the first fluid path and the second fluid path may occur within the fluidic switch in this embodiment, whereas the entire rest of the first flow path and the second flow path may be fluidically (and spatially) separated from each other. This may provide the advantage that pressures, flow rates, separation procedures and/or any other parameters or properties within the first flow path and the second flow path can be adjusted independently. Hence, the flow paths of first and second dimensions may be always separate from each other and never crossing, except the transfer provided by the valve. In such an embodiment, the valve provides the fluid transfer between the two dimensions, but at no time the flow paths of first and second dimensions are actually connected with each other.

According to an exemplary embodiment of the invention, the fluidic switch is switchable between different fluid switching states for transferring first fluid from the first flow path into the second flow path in such a manner that in a transition period during switching between the different fluid switching states fluid flow along the first flow path and along the second flow path continues uninterrupted. More particularly, the fluidic switch may be configured for being switchable between a plurality of fluid switching states (for instance corresponding to different relative positions between a stator and a movable member, such as a rotor of a fluidic valve as an embodiment of the fluidic switch) so that a fluid flow through the fluid processing device is never interrupted. For example, the fluidic switch may comprise at least one fluidic valve having a stator and a movable member being movable (in particular rotatable) relative to the stator. The stator may have a plurality of fluidic ports connected to various fluidic members of the fluid processing device, in particular also providing for a fluidic coupling with the first flow path and the second flow path. The movable member may comprise grooves or other fluid conduits which, by moving the movable member relative to the stator between different fluid switching states, can fluidically couple or decouple respective ones of the ports. During a transition of such a fluidic valve from one fluid coupling state to another one, the movable member has to move by a certain extent so as to bring another groove or fluid conduit in fluid coupling connection with respective ones of the ports. Conventionally, such a transition period may involve a temporary flow blockade or decoupling of the first flow path with regard to a fluid destination of the first fluid flowing along the first flow path so that the first fluid accumulates upstream of the fluidic valve and causes a pressure increase. This may harm fluidic components in the first flow path, in particular a detector upstream of the fluidic switch. Exemplary embodiments of the invention however provide a fluidic switch which is configured in a way that even during such a transition period the fluid flow is continuously guaranteed.

According to an exemplary embodiment of the invention, the fluid processing device further comprises a first fluid accommodation volume, a second fluid accommodation volume and a third fluid accommodation volume each of which having fluidic interfaces fluidically coupled to the fluidic switch and being configured for cooperating to maintain a fluid flow along the first flow path and along the second flow path (wherein the first flow path and the second flow path may remain without immediate connection to one another) via at least one of the fluid accommodation volumes while the fluidic switch is switched for transferring first fluid from the first flow path into the second flow path, in particular by connecting a fluid accommodation volume, containing a fluid from the first flow path, into a second flow path. By the provision of three such fluid accommodation volumes, for example sample loops each connected to two assigned ports of the fluidic switch, may be implemented as fluid accommodation volumes or bypass paths which can be selectively brought in fluid communication with certain sections of the first flow path or the second flow path, respectively, to prevent interruption of the continuous flow in any of the flow paths upon switching.

According to an exemplary embodiment of the invention, the fluidic switch is configured to be switchable into a fluid processing switching state in which the first flow path includes the first fluid accommodation volume or the second fluid accommodation volume, while the second flow path includes respectively the other one (i.e. the first fluid accommodation volume or the second fluid accommodation volume), and while none of the first flow path and the second flow path includes the third fluid accommodation volume (see for instance FIG. 2 and FIG. 3). In this fluid processing switching state, first fluid which has been temporarily stored in the first or the second fluid accommodation volume may be introduced into the second flow path, for example for analysis (for instance separation). Such an analysis may involve the separation of this portion of the first fluid in the second flow path into fractions. For instance, a chromatographic separation may take place in this fluid processing switching state. By alternately coupling the first fluid accommodation volume or the second fluid accommodation volume with the second flow path, a very efficient and fast analysis of the first fluid in the second flow path can be accomplished with very short dead times.

According to an exemplary embodiment of the invention, the fluidic switch is configured to be switchable in a first fluid splitting switching state in which the first flow path includes both the first fluid accommodation volume and the second fluid accommodation volume while the second flow path includes the third fluid accommodation volume (see for instance FIG. 4). In this first fluid splitting switching state, the first fluid flow is split in the first flow path into two parallel flow portions flowing in parallel through the first fluid accommodation volume and the second fluid accommodation volume while at the same time the second fluid flows through the third fluid accommodation volume. This operation mode may also be denoted as one of operation modes of the fluidic switch.

According to an exemplary embodiment of the invention, the fluidic switch is configured to be switchable in a second fluid splitting switching state in which the first flow path includes the first fluid accommodation volume or the second fluid accommodation volume while the second flow path includes respectively the other one (i.e. the first fluid accommodation volume or the second fluid accommodation volume) and includes the third fluid accommodation volume (see for instance FIG. 5 and FIG. 6). As with the fluid processing switching state, also the second fluid splitting switching state can have two (for instance alternatingly activatable) sub-modes: In one of these sub-modes, the first flow path is fluidically coupled with the first fluid accommodation volume only. In the other sub-mode, the first flow path is fluidically coupled with the second fluid accommodation volume only. In parallel, the second flow path is fluidically coupled with both the third fluid accommodation volume and the other one of the first and the second fluid accommodation volumes being presently not in fluid communication with the first flow path. With such a configuration, the second fluid is split between the third fluid accommodation volume and the one of the first and the second fluid accommodation volumes being in fluid communication with the second flow path. This switching mode can also be denoted as an intermediate switching mode in which interruption of the fluid flow is and remains prevented.

According to an exemplary embodiment of the invention, the fluid processing device is configured as a fluid reactor device configured for effecting a reaction of the first fluid with a reaction medium, in particular a reaction medium from a reactor unit (see for instance FIG. 2 to FIG. 6). In such an embodiment, a fluid reactor can be arranged in the first flow path and can be capable of carrying out a for instance chemical or biological reaction with the first fluid. After this reaction, for instance with a certain substance of the fluid reactor, the correspondingly modified first fluid can be, in portions or sections or packets, be introduced into the second flow path, for example for separation of the modified first fluid in fractions, for interaction with another second fluid or for other analysis purposes. In such an embodiment, it may be undesirable that the flow of first fluid along the first flow path is temporarily interrupted by a switching process of the fluidic switch. This might be harmful for fluidic members in a first flow path as well as to a source of the first fluid to the first flow path which may be e.g. an organism connected to the first flow path.

According to another exemplary embodiment of the invention, the fluid processing device is configured as a sample separation device configured for separating the first fluid (see for instance FIG. 7 to FIG. 11). According to this embodiment, the first fluid can be, in packets, introduced into the second flow path to be separated or further separated there. For instance, a chromatographic separation column may be arranged in the second flow path for separating the first fluid into fractions. In this embodiment, the second fluid drive unit driving the second fluid may drive a mobile phase (for instance in accordance with a gradient mode) so as to separate the first fluid in accordance with the principles of liquid chromatography.

According to an exemplary embodiment of the invention, the fluid processing device is configured as a two-dimensional sample separation device configured for separating the first fluid into fractions and at least one of the fractions of the transferred first fluid into sub-fractions. Two separation units may be provided in two consecutive separation stages in such a two-dimensional sample separation system. This means that the sample fluid is first separated in accordance with a first separation criterion, and at least one or some of the fractions resulting from the first separation are subsequently separated in accordance with a second, different, separation criterion ore more finely separated in accordance with the first separation criterion. In this highly preferred embodiment, a first separation of the first fluid into fractions is carried out while the first fluid flows through the first flow path. For this purpose, a first separation unit such as a chromatographic separation column may be provided in the first flow path. A fluidic sample to be separated may be injected by an injector into mobile phase driven by the first fluid drive unit. The mixture of the fluidic sample and the mobile phase, together forming the first fluid, may then be separated, for instance chromatographically, for example by carrying out a gradient run (during which a solvent composition of the mobile phase is modified in accordance with a gradient profile). However, it might be required or desired to further separate the individual fractions in which the fluidic sample has been separated in the first flow path, wherein this second separation can be carried out in the second flow path. To achieve this, packets of the first fluid are to be transferred from the first flow path into the second flow path. This is accomplished by the fluidic switch which may also be denoted as a modulator valve. Conventionally, two-dimensional liquid chromatography may suffer from the fact that, while the modulator valve switches, the first fluid path is temporarily blocked by the fluidic switch. However, the fluidic valve may be configured according to an exemplary embodiment in such a manner that switching of the modulator valve does not result in a temporary flow interruption of first fluid in the first flow path. In two-dimensional liquid chromatography, such conventionally occurring temporary flow interruptions result in a pressure increase upstream of the modulator valve. This may damage a sensitive detector upstream of the fluidic switch and/or other fluidic members. By suppressing such pressure ripples or pressure shocks, in particular such a detector or other fluidic members in the first flow path are protected against a high mechanical load associated with such pressure shocks. Also, pressure dipping may be prevented.

According to an exemplary embodiment of the invention, the fluidic switch is configured for being switchable between a plurality of fluid switching states so that a fluid flow in the first path and a fluid flow in the second path are continuously maintained, i.e. are never interrupted due to blockage of the corresponding flow path. In other words, in none of the fluid switching states, interruption or blockage of the fluid flow along any of the first flow path or the second flow path occurs at any time (in particular also at valve positions between the defined fluid switching states) in this embodiment.

According to an exemplary embodiment of the invention, the fluidic switch is configured for being switchable between a plurality of fluid switching states so that a fluid flow at a fluidic outlet of the first dimension is never interrupted and a fluid flow at a fluidic inlet of the second dimension is never interrupted as well. According to such an embodiment, in addition to the prevention of the interruption of the fluid flow between first flow path and fluidic switch, also continuous supply of fluid at an outlet of the fluid switch into the second flow path is ensured. Therefore, not only the inlet, but also the outlet side of the modulator valve or other type of fluidic switch is prevented from flow interruption, thereby avoiding a negative impact of a switching operation upstream and downstream of the fluidic switch.

According to an exemplary embodiment of the invention, the fluid processing device comprises a separation unit for separating the first fluid in the first flow path upstream of the fluidic switch. Such a separation unit may for instance be a chromatographic separation column. According to an exemplary embodiment of the invention, the fluid processing device further comprises a further separation unit downstream of the second fluid drive unit and being configured for further separating the transferred first fluid. Also such a further separation unit may be a chromatographic column which may have different dimensions from the separation unit in the first flow path.

According to an exemplary embodiment of the invention, the fluid processing device comprises a detector located in the first flow path upstream of the fluidic switch and being configured for detecting the separated first fluid. Such a detector may be a fluorescence detector with a flow cell being specifically sensitive with regard to overpressure. Therefore, ensuring a continuous flow from the first flow path into the second flow path, such a detector may be safely prevented from failure.

According to an exemplary embodiment of the invention, a fluidic short circuit path is integrated in or fluidically coupled to the fluidic switch so as to conduct fluid during a switching interval between different fluid switching states. Such a fluidic short-circuit may be temporarily activated for fluid flow during a switching operation of a fluidic switch and may serve for temporarily accommodating or redirecting fluid which otherwise would be blocked from passing through the fluidic switch during a switching operation.

According to an exemplary embodiment of the invention, the fluidic switch is configured as one of the group consisting of a single fluidic valve, a plurality of cooperating fluidic valves, and at least one fluidic valve comprising one or more sample loops (wherein the switching device or assembly may comprise loops connected between ports of the switching device, or a valve member itself may have incorporated loops) each of which being fluidically connected between two ports of at least one fluidic valve. For instance, FIGS. 12 through 16 show a fluidic valve having all flow interruption prevention functionality integrated so as to achieve the desired effect. FIG. 17 shows a single fluidic valve according to another exemplary embodiment which also fulfils this task. The fluidic valves according to FIGS. 12 through 17 each have three connected fluid accommodation volumes configured as fluid conduits having two fluidic interfaces thereof being coupled to respective ports of the fluidic valve, whereas two of the accommodation volumes may be sample loops and the third accommodation volume may be a temporary switchable short-cut. In FIG. 18, the fluidic switch is realized by two cooperating fluidic valves. FIG. 19 to FIG. 22 shows an embodiment in which the fluidic switch is again realized as a single valve being however free of sample loops as the three above-mentioned fluid accommodation volumes, but having instead of this grooves of the fluidic valve configured as the three fluid accommodation volumes. FIGS. 23 to 27 shows yet another single fluidic valve with three fluidically connected fluid accommodation volumes, again embodied as fluid conduits fluidically connected to ports of the fluidic valve. Oppositely to the exemplary embodiments presented in the FIGS. 12 to 18, the accommodation volumes in the embodiments in the FIGS. 19 to 22 as well as in FIGS. 23 to 27 are all functionally equivalent.

According to an exemplary embodiment of the invention, the fluidic switch is configured for preventing a direct fluidic coupling between the first flow path and the second flow path. According to this highly preferred embodiment, the first flow path and the second flow path remain always fluidically decoupled from one another so that the introduction of the first fluid into the second flow path is not simply accomplished by allowing fluid in the two flow paths to be mixed. This path separation provides a mechanism to maintain a pressure value in the first flow path different from another pressure value in the second flow path. However, despite the maintained separation of the first flow path from the second flow path, exemplary embodiments of the invention nevertheless allow to introduce first fluid into the second flow path without interruption of fluid flow in any of the flow paths.

According to an exemplary embodiment of the invention, the fluid drive unit is configured for driving the fluidic sample and the mobile phase with a pressure of at least 500 bar, in particular of at least 1200 bar, or at least 1300 bar or more. Particularly with such high pressure values, which may occur in modern liquid chromatography apparatuses (such as HPLCs), the generation of a pressure shock in the temporary event of a blocking of fluid flow from the first flow path into the second flow path would generate enormous forces acting on the sensitive fluidic members of the fluid processing device. By preventing undesired fluid flow interruption even under such high pressure conditions, high pressure separation technology can be combined with a high lifetime of the fluidic members.

According to an exemplary embodiment of the invention, the sample separation device is configured as a chromatography sample separation device, in particular a liquid chromatography sample separation device, a gas chromatography sample separation device or a supercritical fluid chromatography sample separation device; or an electrophoresis sample separation device, in particular a capillary electrophoresis sample separation device. However, other sample separation devices can be implemented as well.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference). Embodiments of the present invention might also be embodied based on a device in accordance with the 1260, 1290 Infinity Series.

One embodiment comprises a pumping apparatus as respective fluid drive unit having a piston for reciprocation in a pump working chamber to compress liquid in the pump working chamber to a high pressure at which compressibility of the liquid becomes noticeable.

The separation unit(s) preferably comprise(s) a chromatographic column (see for instance http://en.wikipedia.org/wiki/Column_chromatography) providing the stationary phase. The column might be a glass or steel tube (for instance with a diameter from 50 μm to 5 mm and a length of 1 cm to 1 m) or a microfluidic column (as disclosed for instance in EP 1577012 or the Agilent 1200 Series HPLC-Chip/MS System provided by the applicant Agilent Technologies. For example, a slurry can be prepared with a powder of the stationary phase and then poured and pressed into the column. The individual sample components are retained by the stationary phase differently and separate from each other while they are propagating at different speeds through the column with the eluent. At the end of the column they elute one at a specific time. During the entire chromatography process the eluent might be also collected in a series of fractions. The stationary phase or adsorbent in column chromatography usually is a solid material. The most common stationary phase for column chromatography is based on silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) of the fluid(s) can be either a pure solvent or a mixture of different solvents. It can be chosen for instance to minimize the retention of the compounds of interest and/or the amount of mobile phase to run the chromatography. The mobile phase can also be chosen so that the different compounds can be separated effectively. The mobile phase might comprise an organic solvent like for instance methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The first fluid/sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system may further comprise a detector for detecting separated compounds of the sample fluid, a fractionating unit for outputting separated compounds of the sample fluid, or any combination thereof.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

The separation unit of any of the stages (also called dimensions) may be filled with a separating material. Such a separating material, which may also be denoted as a stationary phase, may be any material which allows a different degree of interaction with sample components so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, carbon, graphite, alumina, zirconia, silicon dioxide, and silica gel, or any of above with a chemically modified (coated, capped etc) surface. However, any packing material can be used that has material properties allowing a sample passing through this material to be separated into different components, for instance due to different degrees of interactions or affinities between the packing material and fractions of the analyte.

At least a part of any of the separation units may be fluid chambers filled with a separating material, wherein the separating material may comprise beads having a size in the range of essentially 0.1 µm to essentially 50 µm. Thus, these beads may be small particles which may be filled inside the separation section of the fluidic device. The beads may have pores having a size in the range of essentially 0.005 µm to essentially 0.2 µm. The fluidic sample may enter the pores, wherein an interaction may occur between the fluidic sample and the inner surface of the pores.

Any of the separation units may be a chromatographic column for separating components of the fluidic sample. Therefore, exemplary embodiments may be particularly implemented in the context of a liquid chromatography apparatus.

The sample separation system may be, in any of its stages, configured to conduct mobile phase through the system by means of a high pressure, particularly of at least 400 bar, more particularly of at least 1000 bar.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIG. 19 to FIG. 22 illustrate different fluid switching states of a fluidic switch of a fluid processing device according to still another exemplary embodiment of the invention.

FIG. 23 to FIG. 27 illustrate different fluid switching states of a fluidic switch of a fluid processing device according to yet another exemplary embodiment of the invention.

Figure 1:
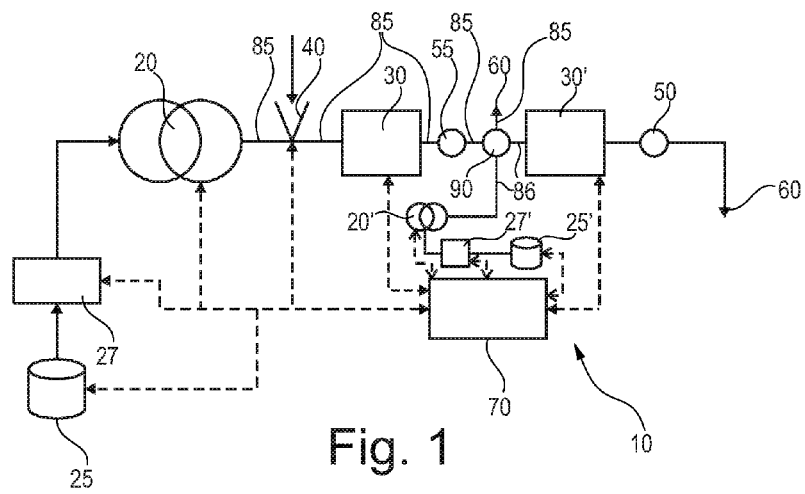
FIG. 1 illustrates a fluid processing device configured as a two-dimensional sample separation device according to an exemplary embodiment of the invention.

The illustration in the drawing is schematic.

Before, referring to the drawings, exemplary embodiments will be described in further detail, some basic considerations will be summarized based on which exemplary embodiments of the invention have been developed.

According to an exemplary embodiment of the invention, a truly un-interrupted fluid flow is accomplished while modulating fluid across multiple dimensions.

When freely allowing any style of combining individual dimensions to form a multi-dimensional liquid chromatography (LC) system, then a user may soon end up with contradicting requirements that may require a compromise. In conventional comprehensive two-dimensional liquid chromatography (2D-LC) it has been a common configuration to have low flow rates in the first dimension and pretty high flow rates for the second dimension. This is due to the fact that it is usually desired to have the second dimension column run as fast as possible to obtain a high first dimension sampling rate, while it may be required that the first dimension separation run is slow enough that a user still can sample each peak several times across its elution width. Conventional heart-cutting 2D-LC often only had one peak or a portion of the peak (heart-cut) spliced into the second dimension, so the modulator valve actually was used only sporadically. But now that multi-heart-cutting 2D-LC is available, a user may face the combination of high flow rates in the first dimension and frequent switching of the modulator valve. This now brings up the necessity to have a modulator valve, which offers flow switching schemes in both individual flow paths, i.e. in the first dimension and in the second dimension. However, it may happen with conventional modulator valves that the first dimension flow and/or the second dimension flow is/are blocked for a certain time during the switching of the modulator valve.

An exemplary embodiment of the invention provides lossless transfer of the fluid from the first dimension to the second dimension without flow interruptions and flow through the second dimension without flow interruptions, which then determines an implementation to be used in the first dimension path, in different words there is no shortcut path in the first dimension at any time, but rather the entire fluid coming out of the first dimension is accommodated in the accommodation reservoirs such as loops and is sequentially portion wise transferred into the second dimension Referring now in greater detail to the drawings, FIG. 1 depicts a general schematic of a liquid separation system as an example for a fluid processing device 10 according to an exemplary embodiment of the invention. A first pump operating as first fluid drive unit 20 receives a mobile phase from a first solvent supply 25, typically via a first degasser 27, which degases the mobile phase and thus reduces the amount of gases dissolved in the mobile phase. The first fluid drive unit 20 drives the mobile phase through a first separating unit 30 (such as a chromatographic column) comprising a stationary phase. A sampling unit or injector 40 can be provided between the first fluid drive unit 20 and the first separating unit 30 in order to subject or add (often referred to as sample introduction) a sample fluid (also denoted as fluidic sample) into the mobile phase. The stationary phase of the first separating unit 30 is configured for separating compounds of the sample liquid.

A second pump, as second fluid drive unit 20', receives another mobile phase from a second solvent supply 25', typically via a second degasser 27', which degases the other mobile phase and thus reduces the amount of gases dissolved in the other mobile phase. By a fluidic switch 90 (here embodied as a fluidic valve), the first dimension (reference numerals 20, 30, . . . ) of the two-dimensional liquid chromatography system of FIG. 1 may be configured to provide fluidic segments or portions to the second dimension (reference numerals 20', 30', . . . ). The fluidic sample is separated into multiple fractions by the first dimension, and each fraction, or a part/slice of it, is modulated into the second separation path and further separated into multiple sub-fractions by the second dimension.

A detector 50 is provided for detecting separated compounds of the sample fluid. An optional further detector 55 is arranged upstream of the fluidic switch 90 and may be used for operating the fluid processing device 10 in a heart-cutting operation. It can however also be used in comprehensive mode as well as in any other operation mode for monitoring or evaluation of the chromatographical data of the first dimension. A fractionating unit can be provided for outputting separated compounds of sample fluid. It is also possible that the processed fluid is pumped towards a waste 60.

While each of the mobile phases can be comprised of one solvent only, it may also be mixed from plural solvents. Such mixing might be a low pressure mixing and provided upstream of the fluid drive units 20, 20', so that the respective fluid drive unit 20, 20' already receives and pumps the mixed solvents as the mobile phase. Alternatively, any of the fluid drive units 20, 20' might be comprised of plural individual pumping units, with the plurality of the pumping units each receiving and pumping a different solvent or mixture, so that the mixing of the mobile phase (as received by the respective separating unit 30, 30') occurs at high pressure and downstream of the respective fluid drive unit 20, 20' (or as part thereof). The composition (mixture) of the mobile phase may be kept constant over time, the so called isocratic mode, or varied over time, the so called gradient mode.

A data processing unit, control unit or processor 70, which can be a conventional PC or workstation, might be coupled (as indicated by the dotted arrows) to one or more of the devices in the fluid processing device 10 in order to receive information and/or control operation. For example, the processor 70 might control operation of the fluid drive units 20, 20' (e.g. setting control parameters) and receive therefrom information regarding the actual working conditions (such as output pressure, flow rate, etc. at an outlet of the pump). The processor 70 might also control operation of the solvent supply 25, 25' (e.g. setting the solvents or solvent mixture to be supplied) and/or the degasser 27, 27' (e.g. setting control parameters such as vacuum level) and might receive therefrom information regarding the actual working conditions (such as solvent composition supplied over time, flow rate, vacuum level, etc.). The processor 70 might further control operation of the sampling unit or injector 40 (e.g. controlling sample injection or synchronization sample injection with operating conditions of the first fluid drive unit 20). The respective separating unit 30, 30' may also be controlled by the processor 70 (e.g. selecting a specific flow path or column, setting operation temperature, etc.), and send—in return—information (e.g. operating conditions) to the processor 70. Accordingly, the detectors 50 and 55 may be controlled by the processor 70 (e.g. with respect to spectral or wavelength settings, setting time constants, start/stop data acquisition), and send information (e.g. about the detected sample compounds) to the processor 70. The processor 70 may also control operation of the fractionating unit (e.g. in conjunction with data received from the detector 50). The processor 70 may include a storage device, which allows to store all or selected information of the analytical process and also to retrieve stored information (which may be advantageous for the above-mentioned scouting operation) from previous analytical processes. The processor 70 may include software or firmware for data evaluation and for providing data evaluation results for further storage or as an output for a human interface.

The first fluid drive unit 20 is hence configured for driving a first fluid (composed of the injected fluidic sample and the mobile phase) along a first flow path 85 which is located partly upstream of the fluidic switch 90 and partly downstream of the fluidic switch 90. The second fluid drive unit 20' is configured for driving a second fluid embodied as a mobile phase along a second flow path 86 which is also located partly upstream of the fluidic switch 90 and partly downstream of the fluidic switch 90. The fluidic switch 90 is fluidically coupled to both the first flow path 85 and to the second flow path 86 (however essentially not directly connecting them fluidically together) and is switchable by the processor 70 for transferring part of the first fluid from the first flow path 85 into the second flow path 86 without interruption of fluid flow along the first flow path 85 and along the second flow path 86 during this switching operation. No direct fluid connection between the first flow path 85 and the second flow path 86 is provided which otherwise would allow for an unlimited substantial direct fluid flow between the two individual flow paths 85, 86. More particularly, the fluidic switch 90 is switchable between different fluid switching states for transferring the first fluid from the first flow path 85 into the second flow path 86 in such a manner that in a transition period during switching between the different fluid switching states fluid flow along the first flow path 85 and along the second flow path 86 continue uninterrupted. The fluid processing device 10 shown in FIG. 1 is configured as a two-dimensional sample separation device configured for separating the first fluid into fractions (which can be detected by detector 55) and at least one of the fractions of the transferred first fluid into sub-fractions (which can be detected by detector 50). The fluidic switch 90 is further configured for being switchable between the plurality of fluid switching states so that the fluid flow at a fluidic outlet of the first dimension (i.e. downstream of detector 55) is never interrupted and a fluid flow at a fluidic inlet of the second dimension (i.e. upstream of the further separation unit 30') is never interrupted. At the same time, the fluidic switch 90 is configured for preventing a direct fluidic coupling (and hence uncontrolled mixing) between the first flow path 85 and the second flow path 86. In other words, there is no direct fluidic connection between the first flow path 85 and the second flow path 86 which may therefore also be at different pressure levels. Embodiments of the fluidic switch 90 are shown in FIG. 12 to FIG. 27.

The separation unit 30 functions as a high fluidic impedance. In other words, the first fluid, which may be constituted by a mixture of fluidic sample and mobile phase, arrives at an inlet of the separation unit 30 with high pressure of for instance several hundred bar. The pressure is significantly reduced while the fluid flows through the separation unit 30. Detector 55 is hence already located in the low pressure regime and usually does not experience high pressure. When however the fluid flows to an inlet of the fluidic switch 90 functioning as modulator valve, a conventionally occurring temporary incapability of the modulator valve to receive new fluid coming from the separation unit 30 would result in a pressure increase at the position of the detector 55 which may damage the detector 55. When however, according to an exemplary embodiment of the invention, the fluidic switch 90 is configured to avoid such a temporary fluidic blockade, the fluid flow from the detector 55 through the fluidic switch 90 is maintained continuously, also during a switch operation of the fluidic switch 90. This protects the fluidic members shown in FIG. 1 from overpressure.

FIG. 2 to FIG. 6 illustrate different fluid switching states of a fluid processing device 10 according to an exemplary embodiment of the invention. This fluid processing device 10 is configured as a fluid reactor device configured for effecting a reaction of the first fluid with a reaction medium of a reactor unit 206 arranged in the first flow path 85 upstream of the fluidic switch 90. After the first fluid has undergone a reaction in the reactor unit 206, a portion of this first fluid is subsequently transferred into the second flow path 86 for analysis, in particular for separation analysis using separation unit 30' arranged in the second flow path 86 downstream of the fluidic switch 90. While the portion of the first fluid transferred into the second flow path 86 flows through the separation unit 30' its fractions can be chromatographically trapped and can be subsequently individually released from the separation unit 30' by conducting a gradient profile of mobile phase through the separation unit 30' under the control of the second fluid drive unit 20'. Such an analysis in the second flow path 86 is however optional.

In the fluid processing device 10 shown in FIGS. 2 to 6, the first fluid flowing along first flow path 85 shall be brought in interaction with a medium or substrate in reactor unit 206 so as to initiate or trigger a for instance chemical (or biological) reaction between the first fluid and the reactor unit 206. Subsequently, the so modified first fluid shall be introduced in packets into the second flow path 86 for analysis by separation unit 30'. Thus, the different fluidic fractions in the manipulated first fluid shall be analyzed, for instance by liquid chromatography, in the separation unit 30'. For this purpose, packets of the manipulated first fluid are temporarily stored in the first or second accommodation volumes 200, 202 and are subsequently introduced, after switching of the fluidic switch 90, in the second flow path 86. Additionally, a third fluid accommodation volume 204 is provided and is connected to two ports of the fluidic switch 90.

Figure 2:
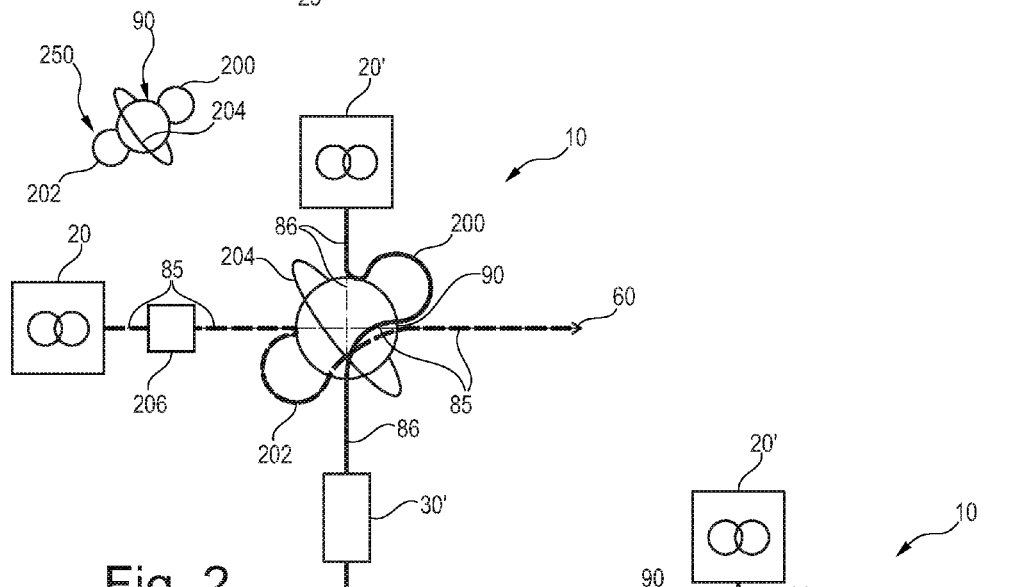
FIG. 2 to FIG. 6 illustrate different fluid switching states of a fluid processing device, comprising a reactor unit, according to an exemplary embodiment of the invention.

The fluid processing device 10 schematically shows construction and fluidic connection of the fluidic switch 90, as can be taken from a detail 250 in FIG. 2. A first fluid accommodation volume 200, a second fluid accommodation volume 202 and a third fluid accommodation volume 204, here each being configured as capillary sections, are fluidically coupled to respectively two fluidic ports of the fluidic switch 90. The fluid accommodation volumes 200, 202, 204 are configured for cooperating to maintain a fluid flow independently along the first flow path 85 and along the second flow path 86 via the fluid accommodation volumes 200, 202, 204 while the fluidic switch 90 is switched for transferring first fluid from the first flow path 85 into the second flow path 86. This will be described in the following referring to FIG. 2 to FIG. 6. The respective fluidic connections of the first flow path 85 and the second flow path 86 with regard to fluidic bridges within the fluidic switch 90 are indicated with a bold line (relating to the second flow path 86) and a dotted line (relating to the first flow path 85), respectively, according to FIG. 2 to FIG. 6.

Figure 3:
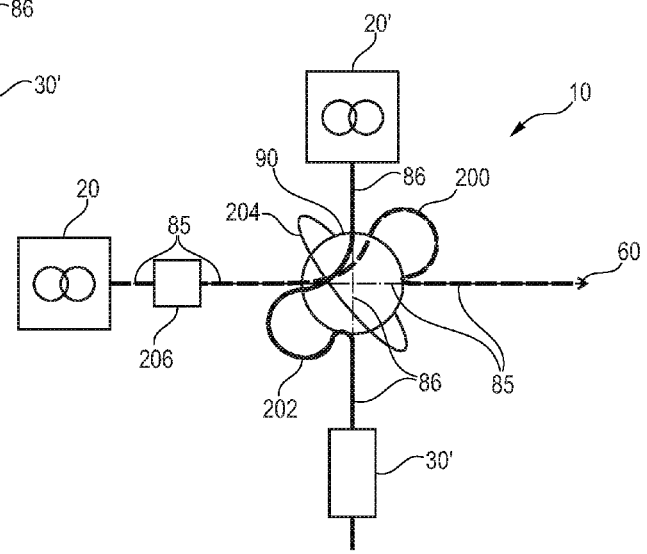

Each of FIG. 2 and FIG. 3 shows the fluidic switch 90 in a fluid processing switching state in which the first flow path 85 includes one of the first fluid accommodation volume 200 and the second fluid accommodation volume 202 (i.e. second fluid accommodation volume 202 according to FIG. 2, and first fluid accommodation volume 200 according to FIG. 3) while the second flow path 86 includes the respectively other one of the first fluid accommodation volume 200 and the second fluid accommodation volume 202 (i.e. second fluid accommodation volume 202 according to FIG. 3, and first fluid accommodation volume 200 according to FIG. 2). None of the first flow path 85 and the second flow path 86 includes the third fluid accommodation volume 204 in this fluid processing switching state, so that the third fluid accommodation volume 204 is temporarily inactive. In the fluid processing switching state, a portion of the first fluid which has been previously filled into the first fluid accommodation volume 200 (see FIG. 2) or in the second fluid accommodation volume 202 (see FIG. 3) is pumped by the second fluid drive unit 20' towards the separation unit 30' for separation and further analysis.

According to FIG. 2, manipulated first fluid which has been introduced into first fluid accommodation volume 200 beforehand is properly analyzed in the second flow path 86. For this purpose, the second fluid drive unit 20' drives a mobile phase and carries the manipulated first fluid temporarily accommodated in the first fluid accommodation volume 200 through the separation unit 30' towards a detector (not shown) in the second flow path 86. Thus, an analysis of the manipulated first fluid is carried out according to FIG. 2. The same holds for FIG. 3 which differs from FIG. 2 in that the manipulated first fluid has been temporarily stored in the second fluid accommodation volume 202 and is now transported towards the separation unit 30' in the second flow path 86.

Figure 4:
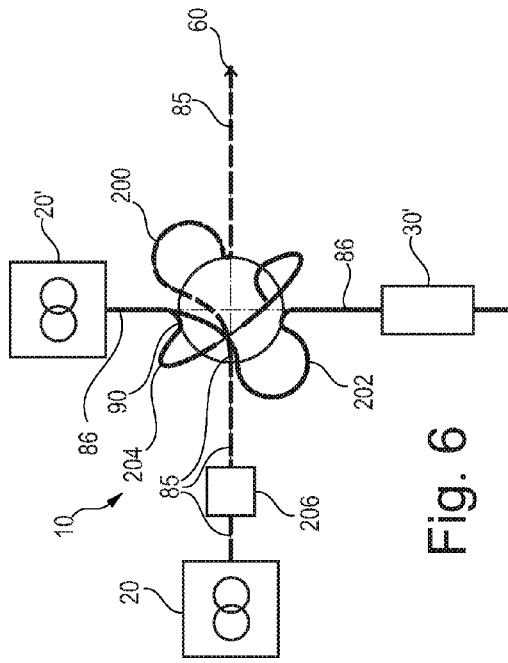

Now referring to FIG. 4, the fluidic switch 90 is configured to be switchable in a first fluid splitting switching state in which the first flow path 85 includes both the first fluid accommodation volume 200 and the second fluid accommodation volume 202 while the second flow path 86 includes the third fluid accommodation volume 204. In this first fluid splitting switching state, the third fluid accommodation volume 204 (which may also be denoted as jumper loop) is now in an active state. Both the first fluid accommodation volume 200 and the second fluid accommodation volume 202 are filled with first fluid according to FIG. 4. According to FIG. 4, the first fluid flowing from the first flow path 85 into the fluidic switch 90 is split to flow partially through the first fluid accommodation volume 200 and partially through the second fluid accommodation volume 202. At the same time, the second fluid flows from the second flow path 86 via the fluidic switch 90 through the third fluid accommodation volume 204.

Figure 5:
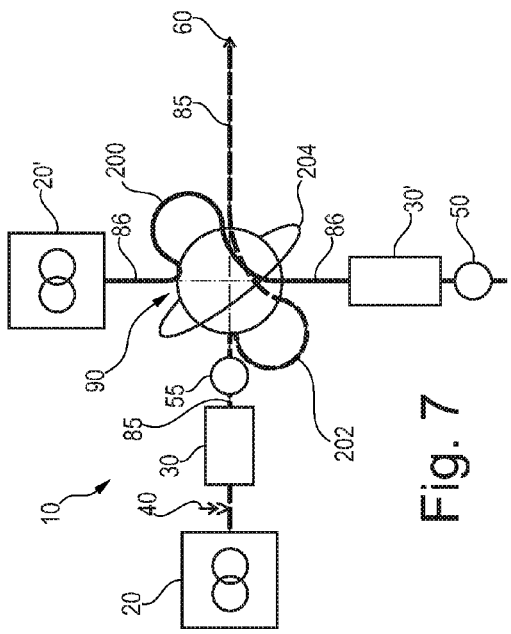
Figure 6:
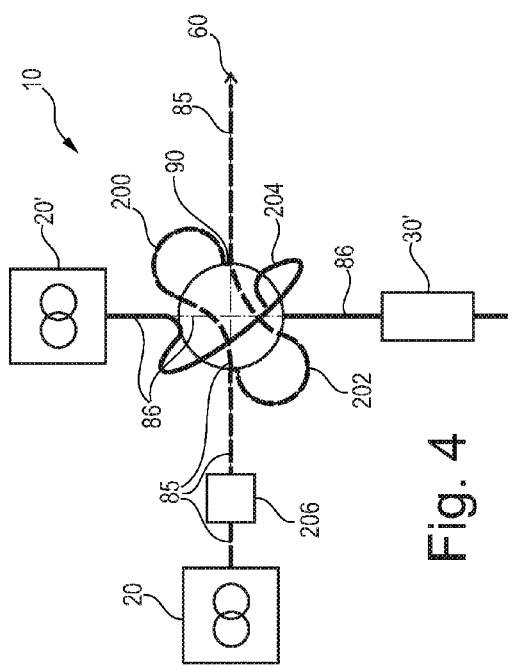

As can be taken from FIG. 5 and FIG. 6, the fluidic switch 90 is further configured to be switchable in a second fluid splitting switching state in which the first flow path 85 includes one of the first fluid accommodation volume 200 or the second fluid accommodation volume 202 (the first fluid accommodation volume 200 according to FIG. 6, and the second fluid accommodation volume 202 according to FIG. 5) while the second flow path 86 includes the respectively other one of the first fluid accommodation volume 200 or the second fluid accommodation volume 202 (the first fluid accommodation volume 200 according to FIG. 5, and the second fluid accommodation volume 202 according to FIG. 6) and includes the third fluid accommodation volume 204. The second fluid splitting switching state takes care that the flow is never interrupted neither along the first flow path 85 nor along the second flow path 86. The second fluid splitting according to FIG. 5 or FIG. 6 is assumed when switching between the fluid processing switching state according to FIG. 2 or FIG. 3 and the first fluid splitting switching state according to FIG. 4. In FIG. 5 and FIG. 6, the first fluid from the first flow path 85 flows through one of the first and the second fluid accommodation volume 200, 202, while the second fluid flows from the second flow path 86 and splits into a first portion flowing through the third fluid accommodation volume 204 and another portion flows through the respective one of the first and the second fluid accommodation volumes 200, 202 which is presently not used by the first fluid. Once a fluid from the first flow path 85 was contained in the fluid accommodation volumes 200, 202, it gets displaced out of that accommodation volume and mixed with the fluid from third fluid accommodation volume 204 within the second flow path 86. By the intermediate states shown in FIG. 5 and FIG. 6, it is prevented that at any time the fluid flow in any of the first flow path 85 or the second flow path 86 is interrupted.

As can be taken from FIG. 2 to FIG. 6, the third fluid accommodation volume 204 is either inactive or is part of the second flow path 86, while never being part of the first flow path 85. While no interruption occurs in the second flow path 86, the first fluid flowing along the first flow path 85 is transferred into the second flow path 86 (which occurs post the switch of the valve). If such switching operations are accomplished systematically and so frequent, that the reservoir (i.e. fluid accommodation volumes 202 or 200) switched into the first flow path 85 is switched out of the first flow path 85 and into the second flow path 86 before its entire volume is flushed with the fluid flowing in the first flow path 85, then the entire fluid from the first flow path 85 gets losslessly transferred to the second flow path 86. The fluid flowing out of the respective accommodation volume towards the waste 60 is then always the fluid, which was within the respective accommodation volume at the moment when the respective accommodation volume was switched into the first flow path 85; typically it is then the historic fluid from the second flow path 86. Thus, it is advantageous to not use the shortcut in the first flow path 85, because the fluid entering the shortcut would have no chance to be transferred to the second flow path 86 and thus the transfer from the first flow path 85 to the second flow path 86 would not be lossless.

FIG. 7 to FIG. 11 illustrate different fluid switching states of a fluid processing device 10 configured as two-dimensional separation device according to another exemplary embodiment of the invention.

FIG. 7 to FIG. 11 show operation modes of the illustrated fluid processing device 10 corresponding to the operation modes shown in FIG. 2 to FIG. 6. However, the fluid processing device 10 according to FIG. 7 to FIG. 11 relates to two-dimensional sample separation. In a first separation dimension, mobile phase is pumped by the first fluid drive unit 20 and the fluidic sample is added to it in the injector 40. The first fluid containing fluidic sample and the mobile phase is then separated into fractions in the separation unit 30. In the case where a detector unit 55 is used in the first dimension (i.e. first flow path 85), the separated fractions are detected by the detector 55 upstream of the fluidic switch 90. When such fractions shall be analyzed in further detail and shall be further separated in sub-fractions, the fluidic switch 90 is switched accordingly so that a certain fluid packet of first fluid is introduced into the second flow path 86. Here, the second fluid drive unit 20' drives a further mobile phase which may be mixed and transported together with the first fluid transferred from the first dimension to the second dimension. The packet of the first fluid is therefore separated by the further separation unit 30' in its sub-fractions, which can subsequently be detected by the detector 50.

According to FIG. 7 to FIG. 11, undesired pressure shocks or pressure fluctuations having a negative impact in particular on detector 55 are prevented by the capability of the fluidic switch 90 to permanently maintain the fluid flow along the first flow path 85 and the second flow path 86 which are nevertheless never in direct fluidic coupling.

Figure 7:
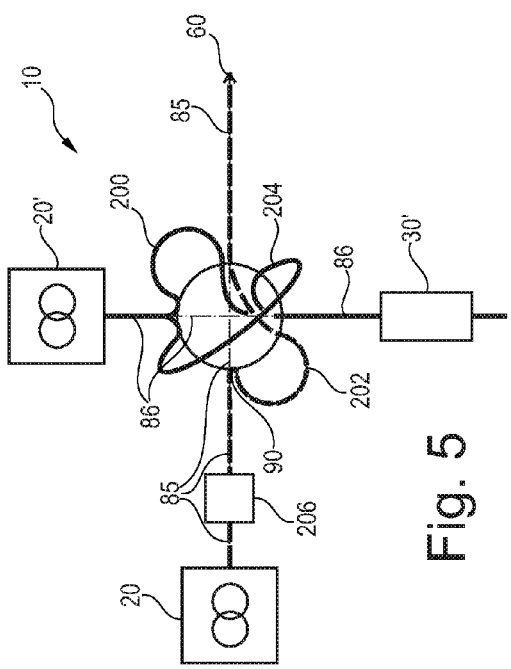
FIG. 7 to FIG. 11 illustrate different fluid switching states of a fluid processing device, adapted for fluid separation, according to another exemplary embodiment of the invention.
Figure 8:
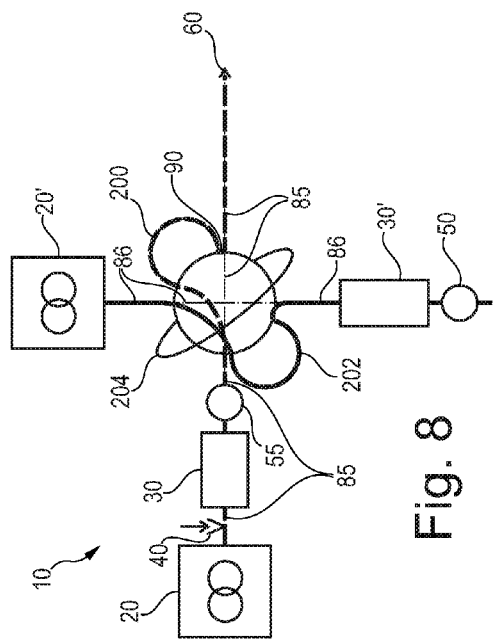
Figure 9:
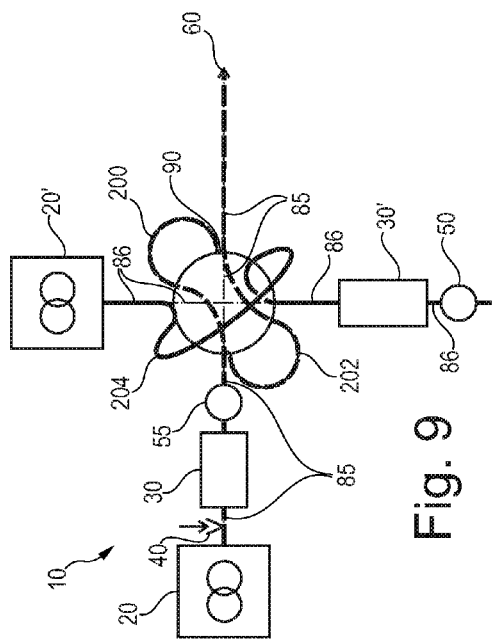
Figure 10:
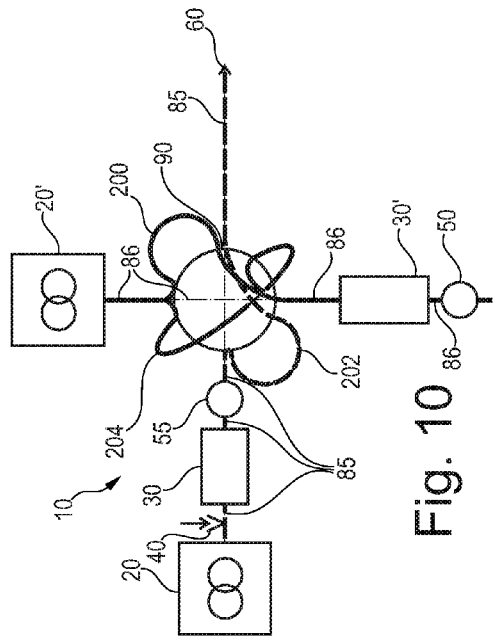
Figure 11:
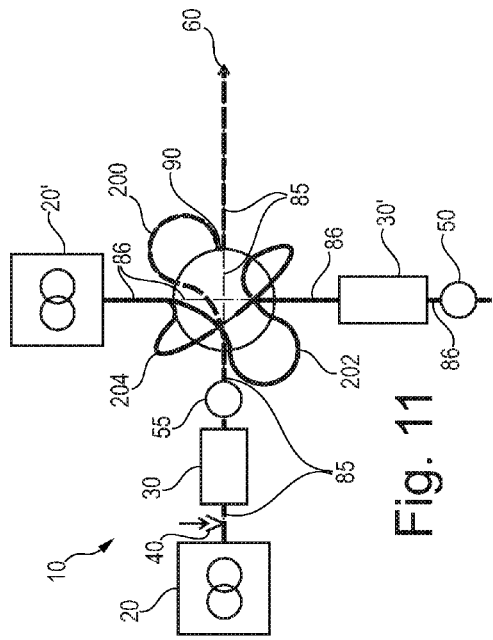

Specifically the sequence of the switching states may be described as: FIG. 7->FIG. 10 (shortcut in form of the third fluid accommodation volume 204 is added to the second flow path 86)->FIG. 9 (first fluid accommodation volume 200 swapped to first flow path 85)->FIG. 11 (second fluid accommodation volume 202 swapped to the second flow path 86)->FIG. 8 (third fluid accommodation volume 204 taken from second flow path 86). Hence, rather than just replacing the first fluid accommodation volume 200 by the third fluid accommodation volume 204, a new connection may be first established, and then the previous one is broken.

Figure 12:
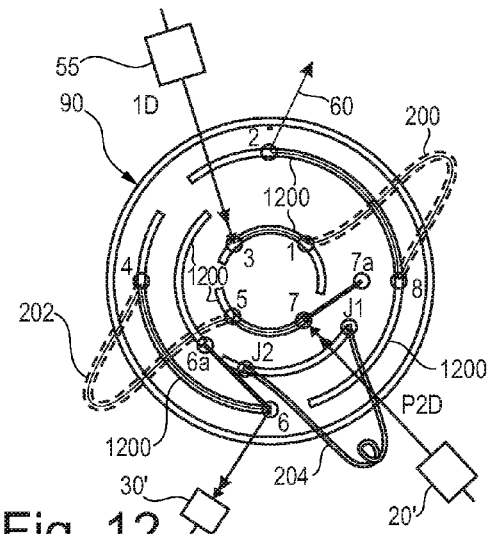
FIG. 12 to FIG. 16 illustrate different fluid switching states of a fluidic switch of a fluid processing device according to an exemplary embodiment of the invention.

FIG. 12 to FIG. 16 illustrate different fluid switching states of a fluidic switch 90 of a fluid processing device 10 according to an exemplary embodiment of the invention. According to FIG. 12 to FIG. 16, the fluidic switch 90 is realized as a single fluidic valve. This fluidic valve comprises a stator and a rotor being rotatable relative to one another. The stator has various fluidic ports denoted with 1 to 8, 6a, 7a, J1, J2. The rotor has various grooves 1200 (a number of curved grooves, realized in circular arc shape in this embodiment). The ports 6a, 6 and ports 7a, 7, respectively are connected (as depicted by straight lines) by either grooves or channels in the stator or by an external capillary connection. By rotating the rotor relative to the stator, the different fluid coupling states according to FIG. 12 to FIG. 16 can be achieved. In FIG. 12, the detector 55, the second fluid drive unit 20' and the further separation unit 30' are indicated so as to clarify the fluidic connections of the various ports of the fluidic switch 90 according to FIG. 12 to FIG. 16. With the fluidic switch 90 according to FIG. 12 to FIG. 16, any flow interruption in a respective one of the above-mentioned flow paths 85, 86 can be prevented. Hence, switching the fluidic switch according to FIG. 12 to FIG. 16 advantageously does not generate an excessive pressure fluctuation downstream of the detector 55.

Figure 13:
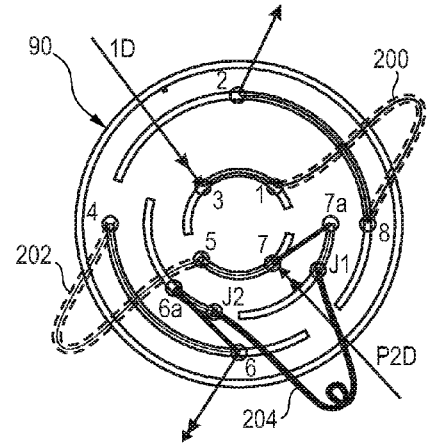
Figure 14:
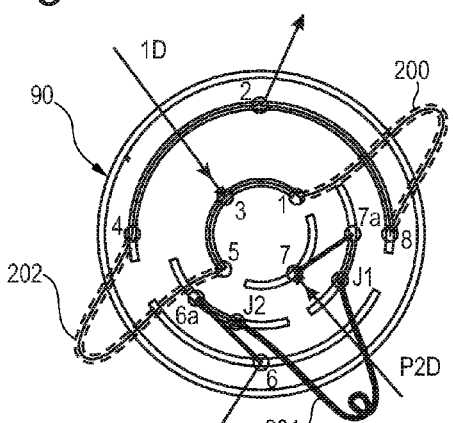
Figure 15:
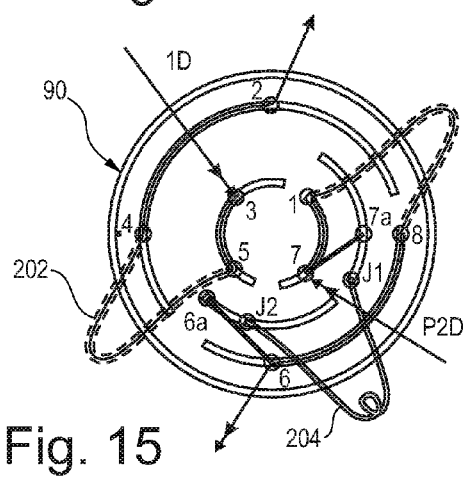
Figure 16:
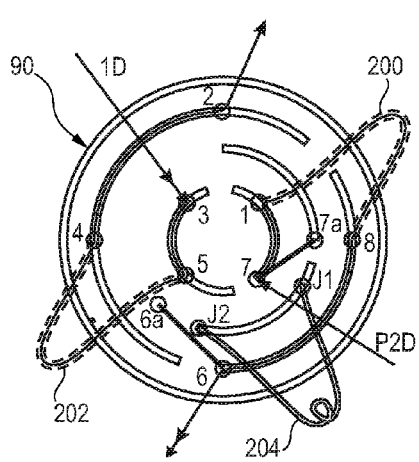
Figure 17:
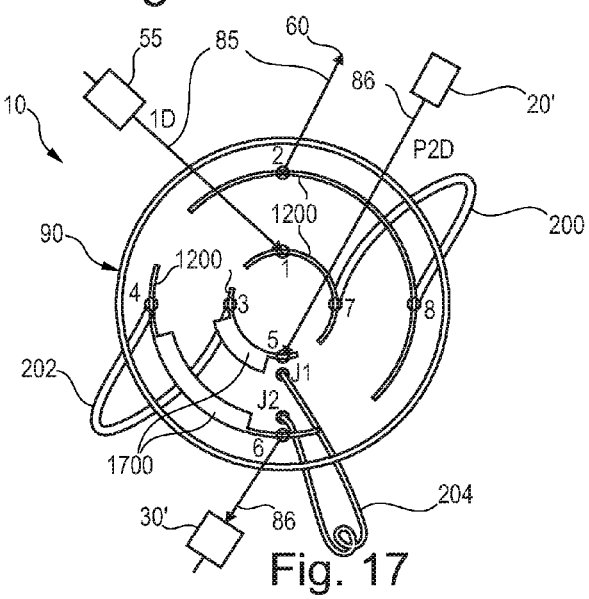
FIG. 17 illustrates a fluidic switch of a fluid processing device according to another exemplary embodiment of the invention.

FIG. 12 to FIG. 16 show the sequential switching phases of such an embodiment in which the switching order is from FIG. 12 to FIG. 13, further to FIG. 14, via FIG. 15 and then to FIG. 16. Hence, the following switching states are assumed:

FIG. 12 (corresponding to FIG. 3 and FIG. 8): left loop (second fluid accommodation volume 202) in the second dimension, right loop (first fluid accommodation volume 200) in the first dimension, third accommodation volume 204 not included in any path FIG. 13 (corresponding to FIG. 6 and FIG. 11): left loop (second fluid accommodation volume 202) in parallel with the jumper loop (third fluid accommodation volume 204) in the second dimension, right loop (first fluid accommodation volume 200) in the first dimension FIG. 14 (corresponding to FIG. 4 and FIG. 9): jumper loop (third fluid accommodation volume 204) alone in the second dimension, both loops (i.e. first fluid accommodation volume 200 and second fluid accommodation volume 202) in the first dimension FIG. 15 (corresponding to FIG. 5 and FIG. 10): right loop (first fluid accommodation volume 200) in parallel with the jumper loop (third fluid accommodation volume 204) in the second dimension, left loop (second fluid accommodation volume 202) in the first dimension FIG. 16 (corresponding to FIG. 2 and FIG. 7): right loop (first fluid accommodation volume 200) in the second dimension, left loop (second fluid accommodation volume 202) in the first dimension, third accommodation volume 204 not included in any path FIG. 17 illustrates a fluidic switch 90, also embodied as a single fluidic valve, of a fluid processing device 10 according to another exemplary embodiment of the invention.

According to FIG. 17, two sectors 1700 of the grooves of the fluidic switch 90 according to FIG. 17 are thicker than other grooves 1200 so that they can be fluidically coupled by different ports of the fluidic switch 90 in different operation modes. For example, one of the grooves with thicker sectors 1700 can fluidically connect to ports 3, 5, 7, but also J1. The other one of the grooves with thicker sectors 1700 can fluidically connect to ports 4, 6, 8, but also J2. This simplifies the design and the complexity of the fluidic switch 90 according to FIG. 17. Evidently enough in both embodiments (FIGS. 12 to 16 and FIG. 17) the third fluid accommodation volume 204 (which may also be denoted as jumper) may be implemented switchable only at one of its ends, whereas the other end may be in a permanent connection with the corresponding fluidic location. For example in the FIG. 17 the port J1 may be fluidically or physically joined with the port 5, such that the flow through the third fluid accommodation volume 204 (jumper) only gets established or disrupted between the ports j2 and 6. A corresponding approach is valid for the FIGS. 12 to 16.

Figure 18:
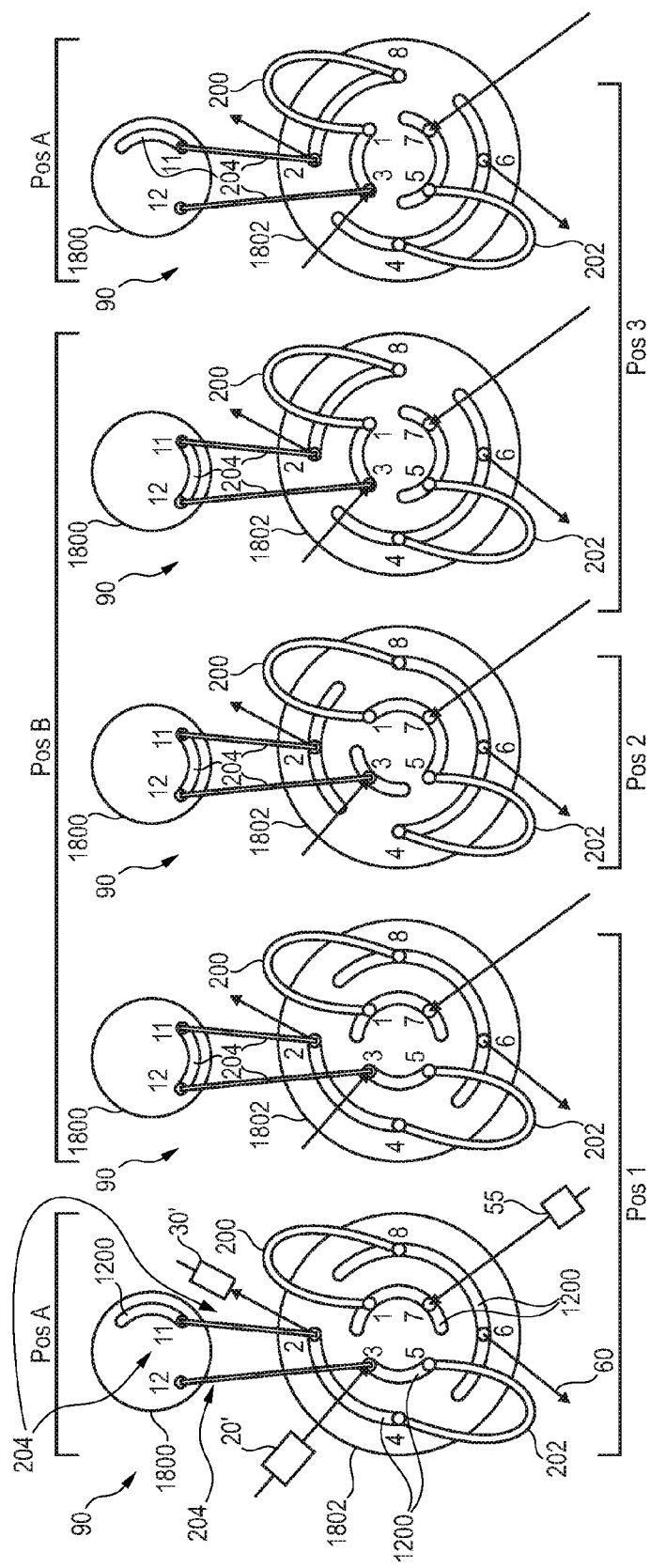
FIG. 18 illustrates a fluidic switch of a fluid processing device according to yet another exemplary embodiment of the invention in different fluid switching states.

FIG. 18 illustrates a fluidic switch 90 of a fluid processing device 10 according to yet another exemplary embodiment of the invention. FIG. 18 shows that the task of switching of both dimensions without interruption in either of those can also be solved by coordinated switching of multiple valves.

FIG. 18 shows five different switching states of a fluidic switch 90 according to yet another exemplary embodiment in which it is realized as a combination of two cooperating fluidic valves 1800, 1802. As can be taken from FIG. 18, the fluidic valve 1802 is of relatively low complexity, and the fluidic valve 1800 is embodied as the simple on/off valve. States of the fluidic valve 1800 are given as positions Pos A/Pos B. States of the fluidic valve 1802 are given as positions Pos 1/Pos 2/Pos 3. According to FIG. 18, the third fluid accommodation volume 204 is embodied as a groove 1200 of the fluidic valve 1800 as well as two connection conduits. For a forward switch sequence, the fluid switching states may change from left to right: First, fluidic valve 1800 switches to Pos B (jumpered). Then fluidic valve 1802 is moved via Pos 2 to Pos 3. Finally, fluidic valve 1800 switches back to Pos A. In case the jumper feature is used for diluting the content of the accommodation volumes 200, 202 with the fluid of the second fluidic path 86 after the accommodation volumes 200 or 202 have been included into the second fluidic path 86, then the combinatory positions Pos B+Pos 1 and Pos B+Pos 3 may be used as specific states for a programmed length of time. The middle position Pos B+Pos 2 is an interim state shown here for explanation of the uninterrupted connectivity in one path (corresponding to the first fluidic path 85) when both the loops are in use for the first dimension (reactor flow path) and connectivity in the other path (i.e. second fluidic path 86) is maintained by the jumper. For the reverse switch sequence, the switching states change from right to left, in reversed order. Alternatively, fluidic valve 1800 can also be a two position/6 port valve or a two position/10 port valve, or of any other kind that contains an additional groove.

Pos A+Pos 3 corresponds to FIG. 7. Pos A+Pos 1 corresponds to FIG. 8. Pos B+Pos 2 corresponds to FIG. 9. Pos B+Pos 1 corresponds to FIG. 11. Pos B+Pos 3 corresponds to FIG. 10.

FIG. 19 to FIG. 22 illustrates different switching states of a fluidic switch 90 of a fluid processing device 10 according to still another exemplary embodiment of the invention. In this alternative implementation, there is no predesignated jumper loop. In this case the fluidic valve constituting fluidic switch 90 has (at least) three identical loop pathways. The valve moves in 120° increments. In contrast to the previous embodiments, in this case the grooves 1200 are static (implemented in the stator), while loop grooves 1900 are implemented as mostly identical features (marked I, II, III) in the rotor. Substantially, loop grooves 1900 are functioning as accommodation volumes. According to FIG. 19 to FIG. 22, a single fluidic valve is shown which constitutes the fluidic switch 90. All three fluid accommodation volumes are provided as radial grooves 1900 in the rotor of the shown fluidic valve and are equivalent in terms of their function. Moreover, in the presently described embodiment there are three main states rather than two main states as in the previously described embodiments.

Initially the loop I is in one path, and the loop II is in the other path (FIG. 19). Switching states follow a sequence from FIG. 19 via FIG. 20, FIG. 21 to FIG. 22. First, one path is bridged by two loops I and III (branched flow), while the other path still passes across the loop II (FIG. 20). In the course of further rotation there are two loops available for the one flow path for bridging the flow (the loop III arrives at the one path). The fresh sample can be brought to the other flow path within the loop I by further rotating the rotor, arriving to the state shown in the FIG. 21. Holding in this position can enable dilution of the sample by parallelizing the flows through the loops I and II, however there is a limitation in this construction in that the dilution-ratio is fixed to 1:1, simply because the loops are all equivalent (FIG. 21). Finally the loop II is driven out of the paths, thus letting the entire flow through the loop I, whereas the other flow passes through the loop III (FIG. 22). In this state the loop III may be accommodating the fresh sample, and the loop I has transferred the previous sample to the other path. Further 120° rotation of the rotor in the same direction would similarly put the loop III (with a fresh sample) into the other path and the loop II into one path. Rotating the valve once more, it is possible to arrive again at the initial state (FIG. 19).

Anyone skilled in the art will understand that there may be any number of loops n>2 used, which would constitute a queue of the samples; the rotation step would then be 360°/n and the grooves correspondingly shorter and closer together on one of the ends.

FIG. 23 to FIG. 27 illustrate different switching states of a fluidic switch 90 of a fluid processing device 10 according to yet another exemplary embodiment of the invention. For instance in a scenario in which it is not desired to have the loops being part of the rotor, it is possible to implement the same switching scheme as shown in the FIGS. 19 to 22 with fixed loops (shown with reference numerals 2200, 2202, 2204 according to FIG. 23 to FIG. 27). This may be accomplished by grooves to connect static in/out connections to the moving groove pattern or any other mechanism to introduce flow continuously over the full rotation, such as axial channels with central port, buried channels etc. FIGS. 23 to 27 show a corresponding embodiment of the invention in which another single fluidic valve is shown as fluidic switch 90. Operation of this embodiment is similar to the described for the FIGS. 19 to 23 and can be derived from FIG. 23 to FIG. 27.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fluid processing device for processing fluid, wherein the fluid processing device comprises:
a first fluid drive unit supported by the fluid processing device and configured for driving a first fluid along a first flow path;
a second fluid drive unit supported by the fluid processing device and configured for driving a second fluid along a second flow path;
a fluidic switch fluidically coupled to the first flow path and to the second flow path and configured for being switchable for transferring the first fluid from the first flow path into the second flow path without interruption of fluid flow along at least one of the first flow path and the second flow path; and
a first fluid accommodation volume, a second fluid accommodation volume, and a third fluid accommodation volume, each of which having fluidic interfaces fluidically coupled to the fluidic switch and being configured for cooperating to maintain a fluid flow independently along the first flow path and along the second flow path via at least one of the fluid accommodation volumes while the fluidic switch is switched for transferring the first fluid from the first flow path into the second flow path.

2. The fluid processing device according to claim 1, wherein the first flow path and the second flow path are fluidically decoupled from each other over their entire lengths, except within the fluidic switch, thereby allowing a transfer of fluid from the first fluid path to the second fluid path only within the fluidic switch.

3. The fluid processing device according to claim 1, wherein the fluidic switch is switchable between different fluid switching states for transferring the first fluid from the first flow path into the second flow path in such a manner that during a transition period that occurs when switching between the different fluid switching states, fluid flow along the first flow path and fluid flow along the second flow path continue uninterrupted.

4. The fluid processing device according to claim 1, wherein the fluidic switch is configured to be switchable in a fluid processing switching state in which the first flow path includes one of the first fluid accommodation volume or the second fluid accommodation volume, while the second flow path includes the respectively other one of the first fluid accommodation volume or the second fluid accommodation volume, while neither the first flow path nor the second flow path includes the third fluid accommodation volume.

5. The fluid processing device according to claim 1, wherein the fluidic switch is configured to be switchable in a first fluid splitting switching state in which the first flow path includes both the first fluid accommodation volume and the second fluid accommodation volume to thereby split the first fluid to flow through the first fluid accommodation volume and through the second fluid accommodation volume, while the second flow path includes the third fluid accommodation volume.

6. The fluid processing device according to claim 1, wherein at least one of the first fluid accommodation volume, the second fluid accommodation volume and the third fluid accommodation volume is configured as one of the group consisting of a capillary section fluidically connected between two fluidic interfaces of the fluidic switch, a groove of a valve member of the fluidic switch, and a channel incorporated into a valve member of the fluidic switch.

7. The fluid processing device according to claim 1, comprising a fluid reactor configured for conducting a chemical, biochemical or biological reaction in the first fluid.

8. The fluid processing device according to claim 1, wherein the fluid processing device is a two-dimensional sample separation device for separating, in a first separation dimension, the first fluid into fractions and, in a second separation dimension, at least one fraction in the transferred first fluid into sub-tractions.

9. The fluid processing device according to claim 8, wherein the fluidic switch is configured for being switchable between a plurality of fluid switching states so that a fluid flow from the first separation dimension into the second separation dimension is permanently maintained permeable.

10. The fluid processing device according to claim 9, wherein the fluidic switch is configured for being switchable between a plurality of fluid switching states so that a fluid flow at a fluidic outlet of the first separation dimension is permanently maintained permeable, and a fluid flow at a fluidic inlet of the second separation dimension is permanently maintained permeable.

11. The fluid processing device according to claim 1, comprising a detector located in the first flow path upstream of the fluidic switch and being configured for detecting separated components or fractions of the first fluid.

12. The fluid processing device according to claim 1, wherein the fluidic switch is configured for being switchable without effecting an excessive pressure change in the first flow path during a switching operation.

13. The fluid processing device according to claim 1, comprising:
a fluidic short circuit path integrated in or fluidically coupled to the fluidic switch so as to conduct fluid during a switching interval between different fluid switching states;
the fluidic switch is configured for being switchable between a plurality of fluid switching states so that a fluid flow through the fluid processing device is permanently maintained permeable.

14. The fluid processing device according to claim 1, wherein the fluidic switch is configured as one of the group consisting of a single fluidic switching device comprising a single fluidic valve with one or more sample loops each of which being fluidically connected between two ports of the fluidic valve, a fluidic switching device comprising a plurality of cooperating fluidic valves with at least one fluidic valve with one or more sample loops each of which being fluidically connected between two ports of the at least one fluidic valve, and a fluidic valve comprising at least three loops incorporated into a movable member of the fluidic valve.

15. The fluid processing device according to claim 1, wherein the fluidic switch is configured for preventing a direct fluidic coupling between the first flow path and the second flow path.

16. The fluid processing device according to claim 1, comprising at least one of the following features:
the fluid processing device comprises a separation unit for separating the first fluid in the first flow path upstream of the fluidic switch;
the fluid processing device further comprises a further separation unit downstream of the second fluid drive unit and configured for further separating the transferred first fluid;
the fluid drive unit is configured for driving the first fluid with a pressure of at least 500 bar;
the fluid processing device is configured as a chromatography sample separation device;
the fluid processing device is configured as an electrophoresis sample separation device;
the fluid processing device comprises an injector configured for injecting a fluidic sample into a mobile phase to thereby compose the first fluid;
the fluid processing device comprises a processor configured to control the fluid processing;
the fluid processing device comprises a processor configured to control switching of the fluidic switch; and
the fluid processing device comprises a degassing apparatus for degassing at least one of the first fluid and the second fluid.

17. A fluid processing device for processing fluid, wherein the fluid processing device comprises:
a first fluid drive unit supported by the fluid processing device and configured for driving a first fluid along a first flow path;
a second fluid drive unit supported by the fluid processing device and configured for driving a second fluid along a second flow path;
a fluidic switch fluidically coupled to the first flow path and to the second flow path and configured for being switchable for transferring the first fluid from the first flow path into the second flow path without interruption of fluid flow along at least one of the first flow path and the second flow path; and
a first fluid accommodation volume, a second fluid accommodation volume, and a third fluid accommodation volume, each of which having fluidic interfaces fluidically coupled to the fluidic switch and being configured for cooperating to maintain a fluid flow independently along the first flow path and along the second flow path via at least one of the fluid accommodation volumes while the fluidic switch is switched for transferring the first fluid from the first flow path into the second flow path,
wherein the fluidic switch is configured to be switchable in a first fluid splitting switching state in which the first flow path includes both the first fluid accommodation volume and the second fluid accommodation volume to thereby split the first fluid to flow through the first fluid accommodation volume and through the second fluid accommodation volume, while the second flow path includes the third fluid accommodation volume,
wherein the fluidic switch is configured to be switchable in a second fluid splitting switching state in which the first flow path includes the first fluid accommodation volume or the second fluid accommodation volume, while the second flow path includes the respectively other one of the first fluid accommodation volume or the second fluid accommodation volume and includes in addition the third fluid accommodation volume to thereby split the second fluid to flow through the other one of the first fluid accommodation volume or the second fluid accommodation volume and in addition through the third fluid accommodation volume.

18. A method of processing fluid, wherein the method comprises:
driving a first fluid along a first flow path;
driving a second fluid along a second flow path; and
switching a fluidic switch, being fluidically coupled to the first flow path and to the second flow path, for transferring the first fluid from the first flow path into the second flow path without interruption of fluid flow along at least one of the first flow path and the second flow path, wherein the fluidic switch comprises:
a first fluid accommodation volume, a second fluid accommodation volume, and a third fluid accommodation volume each of which having fluidic interfaces fluidically coupled to the fluidic switch and being configured for cooperating to maintain a fluid flow independently along the first flow path and along the second flow path via at least one of the fluid accommodation volumes while the fluidic switch is switched for transferring the first fluid from the first flow path into the second flow path.

* * * * *